(12) United States Patent
Sonderegger et al.

(10) Patent No.: US 9,155,876 B2
(45) Date of Patent: Oct. 13, 2015

(54) PORT VALVE OF A BLOOD CONTROL CATHETER

(71) Applicants: Ralph L. Sonderegger, Farmington, UT (US); S. Ray Isaacson, Roy, UT (US)

(72) Inventors: Ralph L. Sonderegger, Farmington, UT (US); S. Ray Isaacson, Roy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 333 days.

(21) Appl. No.: 13/644,200

(22) Filed: Oct. 3, 2012

(65) Prior Publication Data

US 2013/0090609 A1   Apr. 11, 2013

Related U.S. Application Data

(63) Continuation of application No. 61/544,174, filed on Oct. 6, 2011.

(51) Int. Cl.
| | |
|---|---|
| A61M 25/14 | (2006.01) |
| A61M 39/22 | (2006.01) |
| A61M 39/24 | (2006.01) |
| A61M 25/00 | (2006.01) |
| A61M 25/06 | (2006.01) |
| A61M 39/10 | (2006.01) |

(52) U.S. Cl.
CPC ............... *A61M 39/22* (2013.01); *A61M 39/24* (2013.01); *A61M 25/0097* (2013.01); *A61M 25/0606* (2013.01); *A61M 2039/1072* (2013.01); *A61M 2039/1083* (2013.01); *A61M 2039/2433* (2013.01)

(58) Field of Classification Search
CPC .................... A61M 39/045; A61M 2039/062; A61M 2039/064; A61M 2039/1072; A61M 2039/1088; A61M 2039/2433
USPC ........ 604/167.02–167.04, 537, 256, 533, 539
See application file for complete search history.

(56) References Cited

U.S. PATENT DOCUMENTS

| | | | |
|---|---|---|---|
| 4,387,879 A | 6/1983 | Tauschinski |
| 4,449,693 A | 5/1984 | Gereg |
| 4,758,225 A | 7/1988 | Cox et al. |
| 4,773,552 A | 9/1988 | Boege et al. |
| 4,781,702 A | 11/1988 | Herrli |
| 4,809,679 A | 3/1989 | Shimonaka et al. |

(Continued)

FOREIGN PATENT DOCUMENTS

| | | |
|---|---|---|
| CA | 2 133 053 A1 | 3/1995 |
| DE | 20 2009 009 602 U1 | 12/2009 |

(Continued)

OTHER PUBLICATIONS

Elson Silva, PhD, "Respecting Hydrology Science in the Patenting System," pp. 1-7, Jan. 13, 2011.

*Primary Examiner* — Nicholas Lucchesi
*Assistant Examiner* — Justin L Zamory
(74) *Attorney, Agent, or Firm* — Jeanne Lukasavage; Craig Metcalf; Kirton McConkie

(57) ABSTRACT

A catheter assembly is presented which includes a catheter adapter having a blood control valve. A port is disposed in the catheter adapter for providing selective access to the interior of the catheter adapter. A port valve is disposed within the catheter adapter to control access between the interior of the catheter adapter and the port. The port valve includes a flexible tube, a portion of the flexible tube covering an opening between the port and the catheter adapter.

15 Claims, 4 Drawing Sheets

(56) References Cited

U.S. PATENT DOCUMENTS

| | | | |
|---|---|---|---|
| 4,842,591 A | 6/1989 | Luther | |
| 4,874,377 A | 10/1989 | Newgard et al. | |
| 4,917,668 A | 4/1990 | Haindl | |
| 4,935,010 A | 6/1990 | Cox et al. | |
| 4,950,257 A | 8/1990 | Hibbs et al. | |
| 5,041,097 A | 8/1991 | Johnson | |
| 5,053,014 A | 10/1991 | Van Heugten | |
| 5,062,836 A | 11/1991 | Wendell | |
| 5,064,416 A | 11/1991 | Newgard et al. | |
| 5,084,023 A | 1/1992 | Lemieux | |
| 5,085,645 A | 2/1992 | Purdy et al. | |
| 5,098,405 A * | 3/1992 | Peterson et al. | 604/247 |
| 5,108,374 A | 4/1992 | Lemieux | |
| 5,127,905 A | 7/1992 | Lemieux | |
| 5,154,703 A | 10/1992 | Bonaldo | |
| 5,156,596 A | 10/1992 | Balbierz et al. | |
| 5,176,652 A | 1/1993 | Littrell | |
| 5,234,410 A | 8/1993 | Graham et al. | |
| 5,269,771 A | 12/1993 | Thomas et al. | |
| 5,290,246 A | 3/1994 | Yamamoto et al. | |
| 5,295,969 A | 3/1994 | Fischell et al. | |
| 5,330,435 A | 7/1994 | Vaillancourt | |
| 5,350,363 A | 9/1994 | Goode et al. | |
| 5,352,205 A | 10/1994 | Dales et al. | |
| 5,405,323 A | 4/1995 | Rogers et al. | |
| 5,456,675 A | 10/1995 | Wolbring et al. | |
| 5,474,544 A | 12/1995 | Lynn | |
| 5,487,728 A | 1/1996 | Vaillancourt | |
| 5,520,666 A | 5/1996 | Choudhury et al. | |
| 5,549,566 A | 8/1996 | Elias et al. | |
| 5,549,577 A | 8/1996 | Siegel et al. | |
| 5,575,769 A | 11/1996 | Vaillancourt | |
| 5,613,663 A | 3/1997 | Schmidt et al. | |
| 5,651,772 A | 7/1997 | Arnett | |
| 5,657,963 A | 8/1997 | Hinchliffe et al. | |
| 5,697,915 A | 12/1997 | Lynn | |
| 5,730,418 A * | 3/1998 | Feith et al. | 251/149.6 |
| 5,738,144 A | 4/1998 | Rogers | |
| 5,749,861 A | 5/1998 | Guala et al. | |
| 5,806,831 A | 9/1998 | Paradis | |
| 5,817,069 A | 10/1998 | Arnett | |
| 5,833,674 A | 11/1998 | Turnbull et al. | |
| 5,911,710 A | 6/1999 | Barry et al. | |
| 5,954,698 A | 9/1999 | Pike | |
| 5,967,490 A | 10/1999 | Pike | |
| 6,039,302 A | 3/2000 | Cote, Sr. et al. | |
| 6,077,244 A | 6/2000 | Botich et al. | |
| 6,117,108 A | 9/2000 | Woehr et al. | |
| 6,171,287 B1 | 1/2001 | Lynn et al. | |
| 6,273,869 B1 | 8/2001 | Vaillancourt | |
| 6,287,280 B1 | 9/2001 | Lampropoulos et al. | |
| 6,485,473 B1 | 11/2002 | Lynn | |
| 6,575,960 B2 | 6/2003 | Becker et al. | |
| 6,595,981 B2 | 7/2003 | Huet | |
| 6,699,221 B2 | 3/2004 | Vaillancourt | |
| 6,719,726 B2 | 4/2004 | Meng et al. | |
| 6,740,063 B2 | 5/2004 | Lynn | |
| 6,883,778 B1 | 4/2005 | Newton et al. | |
| 7,008,404 B2 * | 3/2006 | Nakajima | 604/158 |
| 7,347,839 B2 | 3/2008 | Hiejima | |
| 7,396,346 B2 | 7/2008 | Nakajima | |
| 7,470,254 B2 | 12/2008 | Basta et al. | |
| 7,736,339 B2 | 6/2010 | Woehr et al. | |
| 7,914,494 B2 | 3/2011 | Hiejima | |
| 2006/0163515 A1 | 7/2006 | Ruschke | |
| 2007/0083157 A1 | 4/2007 | Belley et al. | |
| 2007/0083162 A1 | 4/2007 | O'Reagan et al. | |
| 2007/0233007 A1 | 10/2007 | Adams | |
| 2008/0039796 A1 | 2/2008 | Nakajima | |
| 2008/0108944 A1 | 5/2008 | Woehr et al. | |
| 2008/0287921 A1 | 11/2008 | Bennett | |
| 2009/0287154 A1 | 11/2009 | Harding et al. | |
| 2010/0204648 A1 | 8/2010 | Stout et al. | |
| 2010/0204675 A1 | 8/2010 | Woehr et al. | |
| 2010/0222746 A1 | 9/2010 | Burkholz | |
| 2011/0046570 A1 | 2/2011 | Stout et al. | |
| 2011/0160662 A1 | 6/2011 | Stout et al. | |

FOREIGN PATENT DOCUMENTS

| | | |
|---|---|---|
| EP | 0 369 314 A2 | 5/1990 |
| EP | 0 440 426 A1 | 8/1991 |
| EP | 0 968 736 A1 | 1/2000 |
| EP | 1 129 740 A2 | 9/2001 |
| EP | 1 679 043 A1 | 7/2006 |
| WO | 93/11696 | 6/1993 |
| WO | 96/41649 | 12/1996 |
| WO | 98/00195 | 1/1998 |
| WO | 99/34849 | 7/1999 |
| WO | 99/38562 | 8/1999 |
| WO | 2006/037638 A1 | 4/2006 |
| WO | 2006/059540 A1 | 6/2006 |
| WO | 2007044878 A2 | 4/2007 |
| WO | 2008/014436 A2 | 1/2008 |
| WO | 2008/052790 A2 | 5/2008 |
| WO | 2009/114833 A1 | 9/2009 |
| WO | 2010/093791 A1 | 8/2010 |
| WO | 2012/002015 A1 | 1/2012 |

* cited by examiner

PORT VALVE OF A BLOOD CONTROL CATHETER

RELATED APPLICATION

This application claims the benefit of U.S. Provisional Application No. 61/544,174 filed Oct. 6, 2011, entitled A PORT VALVE OF A BLOOD CONTROL CATHETER, which is incorporated herein by reference.

BACKGROUND

Blood control valves can be use with catheter assemblies or other vascular access devices to prevent undesirable blood exposure from the catheter assembly or from another such vascular access device. Generally, a blood control valve includes the septum and a septum activator. The septum can include a flexible barrier that has one or more slits through which the septum activator can be introduced. In use, the septum activator is advanced through the slit(s) of the septum to selectively open the septum and form a fluid path therethrough. Non-limiting examples of blood control valves are disclosed in the United States Patent Application Publication No. 2011/0046570, filed Aug. 20, 2009, titled "Systems and Methods for Providing a Flushable Catheter Assembly," which is herein incorporated by reference in its entirety.

SUMMARY

The present invention has been developed in response to problems and needs in the art that have not yet been fully resolved by currently available systems and methods. Thus, these systems and methods are developed to provide a side port on a blood control catheter assembly, which includes a catheter assembly having a blood control valve, and a port valve. The port valve can prevent fluids within the catheter assembly from escaping through the side port.

In one aspect of the invention, a catheter assembly includes a catheter adapter, a port disposed on the catheter adapter, and a port valve disposed within the catheter adapter. The catheter adapter has an internal lumen, into which the port opens. The port valve including a flexible tube, a portion of which covers an opening between the port and the internal lumen. The port valve may thus provide one-way selective access to the internal lumen of the catheter adapter via the port.

In another aspect of the invention, catheter assembly includes a catheter adapter, a port disposed on the catheter adapter, and a port valve disposed within the catheter adapter. The catheter adapter has an internal lumen, into which the port opens. The port valve including a flexible tube, a portion of which covers an opening between the port and the internal lumen. The catheter adapter houses a blood control valve that includes a septum activator and a septum. The septum seals a portion of the internal lumen. One or more slits can extend through the septum to provide selective access through the septum. The port valve may thus provide one-way selective access to the internal lumen of the catheter adapter via the port. Moreover, the catheter adapter can provide a port disposed adjacent to the septum activator disposed within the catheter adapter.

Some implementations of the invention include one or more of the following features. The catheter adapter can include a blood control valve disposed within the internal lumen of the catheter adapter. The blood control valve can include a septum and a septum activator. The port valve and the septum can be integrated together. The septum can include a distal barrier surface with a slit extending through it. The flexible tube of the port valve can extend lengthwise along a longitudinal axis of the catheter adapter, and the septum can have a barrier surface that is perpendicular to the longitudinal axis. A portion of the septum activator can be positioned within an inner channel of the flexible tube of the port valve prior to and during septum activation. The inner channel of the flexible tube can have an inner diameter that is greater than an outer diameter of the portion of the septum activator disposed within an inner channel prior to and during septum activation. The port can include a body that is generally oriented substantially perpendicularly to a longitudinal axis of the internal lumen. The flexible tube of the port valve can be a cylindrically-shaped tube. The port valve can be disposed within a recessed portion of the inner surface of the internal lumen of the catheter adapter. The flexible tube of the port valve can be made of silicone, silicone rubber, and/or polypropylene.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
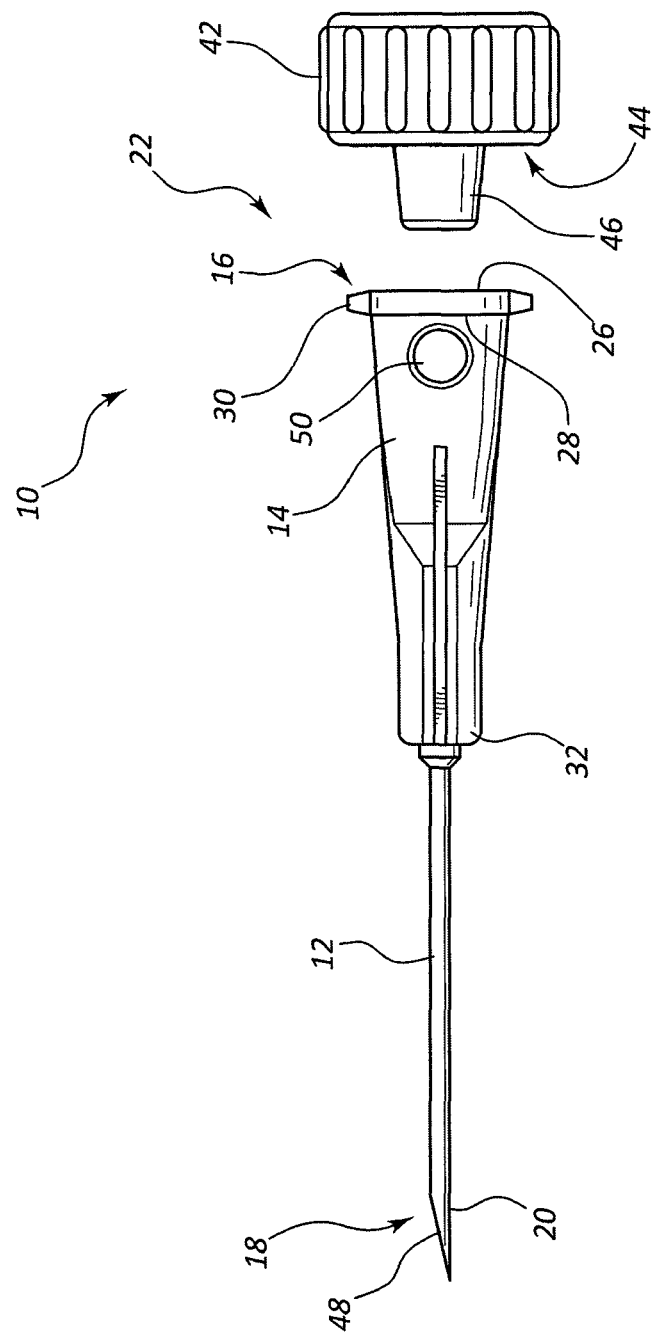
FIG. 1 is a perspective view of a catheter assembly having a port, according to some embodiments.

Referring now to FIG. 1, a catheter assembly 10 is illustrated. The catheter assembly 10 generally includes a catheter 12 coupled to a distal end 32 of a catheter adapter 14. The catheter assembly 10 can be a blood control catheter assembly 10 when it includes a blood control valve therein. The catheter 12 and the catheter adapter 14 are integrally coupled such that an internal lumen 16 of the catheter adapter 14 is in fluid communication with a lumen 18 of the catheter 12. The catheter adapter 14 can include a port 50, which will be described in more detail with reference to FIG. 2. The catheter 12 generally comprises a biocompatible material having sufficient rigidity to withstand pressures associated with insertion of the catheter into a patient. A tip portion 20 of the catheter is generally configured to include a beveled cutting surface 48. The beveled cutting surface 48 is utilized to provide an opening in a patient to permit insertion of the catheter 12 into the vascular system of the patient.

Figure 2:
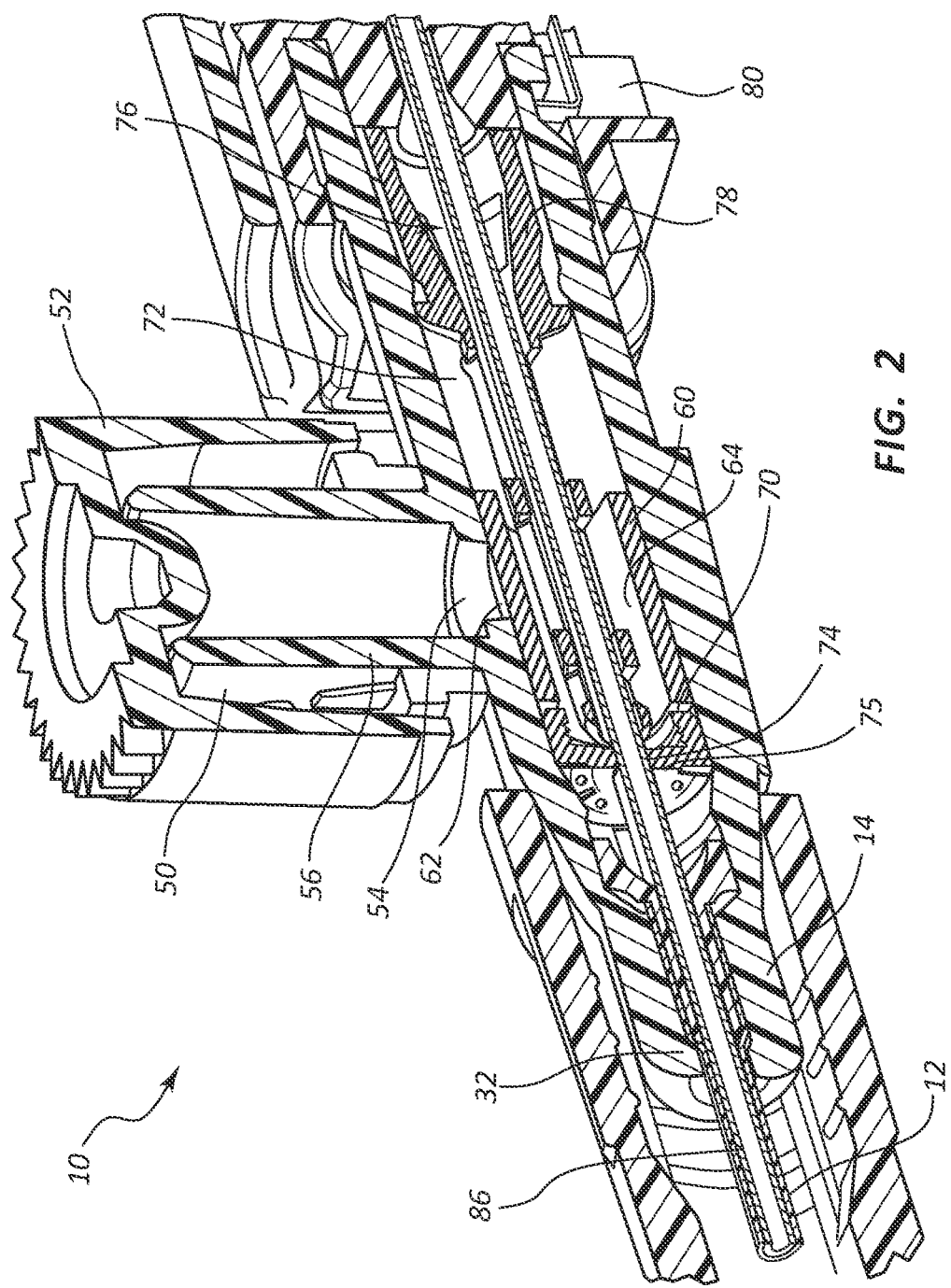
FIG. 2 is a cross-sectioned, perspective view of a catheter assembly having a port and a port valve, according to some embodiments.
Figure 4:
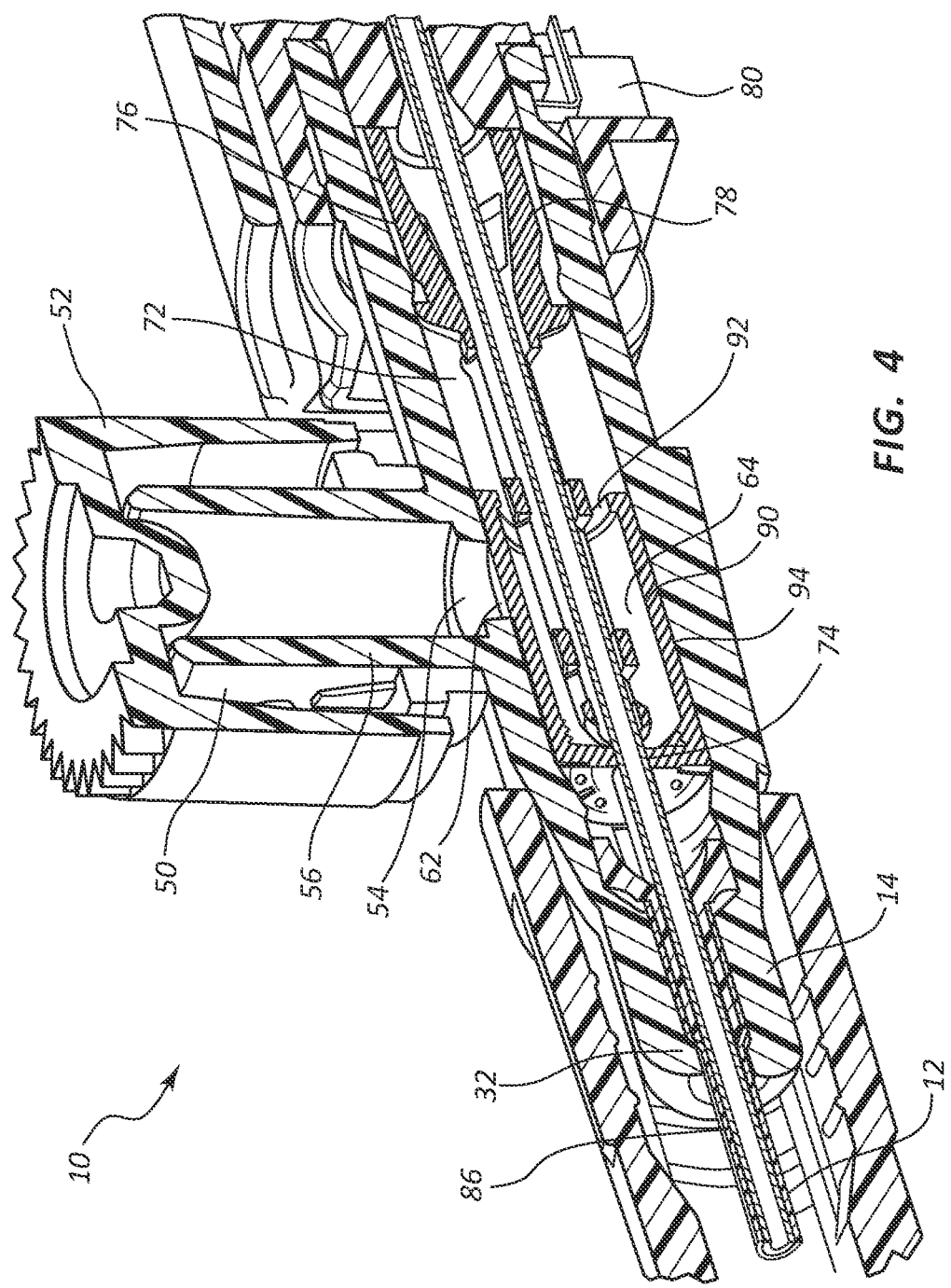
FIG. 4 is a cross-sectioned, perspective view of a catheter assembly having an integrated port valve and septum, according to some embodiments.

One of skill in the art will appreciate that the features of the present invention may be incorporated for use with an over-the-needle catheter assembly, as shown in FIGS. 2 and 4, which can include the tapered end instead of a beveled cutting surface 48. For example, one of skill in the art will appreciate that a flexible or semi-flexible polymer catheter may be used in combination with a rigid needle to enable insertion of the catheter into a patient. One of skill in the art will further appreciate that surgically implanted catheters or other catheter types may also be used.

Once inserted into a patient, the catheter 12 and catheter adapter 14 can provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing to facilitate delivery of a fluid to or removal of a fluid from a patient.

In some embodiments, a proximal end 22 of the catheter adapter 14 includes a flange 28. The flange 28 provides a positive surface that may be configured to enable coupling of intravenous tubing or a conduit coupler 42 to the catheter assembly 10. In some embodiments, the flange 28 includes a set of threads 30. The threads 30 are generally provided and configured to compatibly receive a complementary set of threads 44 comprising a portion of a male luer or conduit coupler 42. The conduit coupler 42 is generally coupled to an end portion of the patient conduit in a fluid-tight manner. In some embodiments, an inner portion of the conduit coupler 42 is extended outwardly to provide a probe surface 46.

In some embodiments, the proximal end 22 to the catheter adapter 14 includes a female luer connector having a female luer taper and/or female luer lock threads. The female luer taper can be disposed at least in part within the proximal portion of the lumen 16 of the catheter adapter 14. Additionally, the flange 28 and/or threads 30 previously mentioned can comprise the female luer lock threads. The female luer connector can thus be configured to connect to a male luer lock or a male luer slip. Each of these components can be sized and configured in conformity with at least some of the International Standards Organization (ISO) standards for female and male luer connections under current or future standards. Accordingly, the proximal end 22 to the catheter adapter 14 can thus be configured to connect to a male luer lock or a male luer slip of the conduit coupler 42, IV line, luer access connector, needle hub, vent plug, or other known or future developed IV device.

The probe surface 46 is generally configured to compatibly insert within a proximal end 22 of the catheter adapter 14. Following insertion of the probe 46 into the proximal end 22 of the catheter adapter 14, the conduit coupler 42 can be rotated to interlock the coupler 42 and the flange 28 (via the sets of threads 30 and 44). During the process of interlocking the conduit coupler 42 and the flange 28, the probe 46 can be advanced into the lumen 16 of the catheter adapter 14 to an inserted position. The inserted position of the probe surface 46 activates the catheter assembly 10 to enable flow of fluid through the catheter 12 and catheter adapter 14. Once the conduit coupler 42 and the catheter adapter 14 are attached, a fluid may be delivered to a patient via the patient conduit and the inserted catheter 12.

Reference will now be made to FIG. 2, which depicts a cross-sectioned view of a catheter assembly 10. As shown, the catheter assembly 10 can include a port 50, such as a side port. The port 50 can have various uses, as known in the art, including for the infusion of fluids into the internal lumen 76 of the catheter adapter 14. Such infusions can flush medicaments and other fluids from the internal lumen 76 and can be used to prime the catheter assembly 10. The port 50 can include an opening 54 disposed between the body 56 of the port 50 and the internal lumen 76 of the catheter adapter 14. The body 56 of the port 50 can extend away from the catheter adapter 14. The port 50 can be covered by a port cover 52 that can prevent contamination and exposure of port 50. Accordingly, in use, a clinician opens the port cover 52 and infuses a fluid into the port 50 through the opening 54 into the internal lumen 76 of the catheter adapter 14. When the fluid infusion is complete, the clinician can close the port cover 52.

As shown in FIG. 2, the catheter adapter 14 can include a blood control valve. As shown the blood control valve can be disposed on a proximal side of the septum. As previously mentioned, the blood control valve can include the septum 70 and a septum activator 72 that opens the septum 70. The septum 70 can include one or more slits 74 through a barrier member 75 of the septum. In some embodiments, the barrier member can be formed in a distal portion of the septum 70. The septum activator 72 can be inserted into the one or more slits 74 during septum activation to establish a fluid path through the septum 70. As also shown, a needle hub 80 can be coupled to the proximal end of the catheter adapter 14, and a needle 86 (e.g., an introducer needle) can extend from the needle hub 80, through the septum 70 and the catheter 12. After proper catheter placement, the needle 86 may be removed from the catheter adapter 14.

In some embodiments, one or more slits 74 within the septum 70 permit passage of the needle 86 through the barrier member 75 of the septum 70, thereby enabling a sharpened tip of the needle 86 to extend distally beyond the tip portion 20 of the catheter 12. As mentioned, following the catheterization procedure, the needle 86 can be removed from the catheter assembly 10 and is safely disposed.

In some embodiments, the needle 86 is coated with a significant amount of silicone or similar fluid, such as fluorosilicone. The purpose of the coating fluid is threefold. Firstly, the coating fluid acts as a lubricant between the outer surface of the needle 86 and the interfacing surfaces of slit 74. Thus, upon withdrawal of the needle 86 from the septum 70, the coating fluid prevents undesirable adhesion between the outer surface of the needle 86 and the interfacing surfaces of slit 74. Secondly, excess coating fluid accumulates within slit 74 thereby assisting in sealing the septum 70 to prevent blood from flowing back through the septum following removal of the needle 86. Excess coating fluid accumulates within slit 74 as needle 86 is removed from catheter assembly 10. In particular, when the needle 86 is being withdrawn through septum 70, the interfacing surfaces of slit 74 act to wipe the coating fluid from the outer surface of the needle 86 thereby displacing the coating fluid into slit 74. Thirdly, the coating fluid acts as a lubricant to prevent undesirable adhesion between opposing surfaces of slit 74.

The coating fluid may include any biocompatible lubricant. In some embodiments, the coating fluid comprises a lubricant such as a non-wetting lubricant that is applied to an interface between the needle 86 and the slit 74 to further eliminate possible leakage of fluid and/or air. A non-wetting lubricant may also be beneficial to prevent tearing or other damage to the slit that may occur when the needle is removed from the catheter assembly following catheterization. A non-wetting lubricant may also facilitate proper realignment of the opposing surfaces of slit 74 following removal of the needle 86. Non-limiting examples of a non-wetting lubricant include known Teflon based non-wetting materials such as Endura, from Endura Coating Co.; A20, E-20, 1000-S20, FEP Green, PTFE and X-40 from Tiodize; Cammie 2000 from AE Yale; 21845 from Ladd Research; MS 122-22, MS 122DF, MS-143DF, MS-122V MS-122VM, MS143V, MS-136W, MS-145W, U0316A2, U0316B2, MS-123, MS-125, MS-322 and MS-324 from Miller-Stepheson; and 633T2 from Otto Bock can also be used. Various non-Teflon based non-wetting lubricant type materials include Dylyn, from ART; Nyebar, Diamonex, NiLAD, TIDLN, Kiss-Cote, Titanium oxide; Flu-ocad Fluorochemical Coating FC-722, from 3M; Permacote from Dupont; Plasma Tech 1633 from Plasma Tech, Inc.; and silicone sprays.

As further shown in FIG. 2, the catheter adapter 14 can also include a port valve 60. In various embodiments, such as that shown, the port valve 60 comprises a generally cylindrical tube. The port valve 60 can be positioned within the internal lumen 76 of the catheter adapter 14 such that an outer surface 62 of the port valve 60 covers the opening 54 of the port 50. Thus positioned, the port valve 60 can prevent fluid from flowing out the port 50 from the internal lumen 76. Furthermore, the port valve 60 can be configured to permit fluid into the internal lumen 76 from the port 50 by at least partially collapsing when fluid is introduced into the port 50.

Accordingly, port valve 60 can be designed to collapse inwardly when a predetermined pressure is applied to the port valve 60 from the opening 54 of the port 50. Predetermined pressure can generally be less than the amount of force pressing against port valve 60 through the opening 54 during an infusion of fluid via the port 50. Accordingly, in various embodiments, the valve 70 is flexible or semi-flexible. The port valve 60 can be made of various flexible or semi-flexible materials including, for example, silicone, silicone rubber, polypropylene, or other suitable materials. The flexibility or rigidity of such materials can affect predetermined pressure required to open the port valve 60. For example, a more flexible material may require a smaller predetermined pressure.

Figure 3:
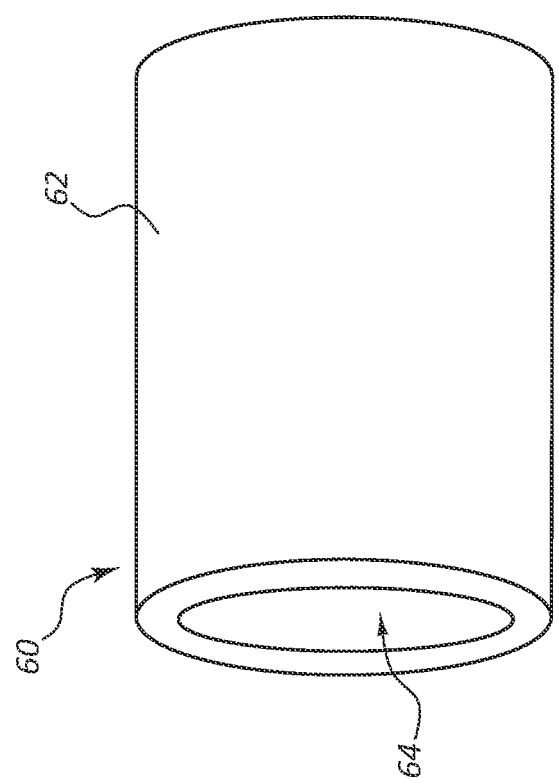
FIG. 3 is a perspective view of a cylindrically-shaped, tubular port valve, according to some embodiments.

As shown, the port valve 60 can have a tube portion that has a generally tubular shape, including, but not limited to a cylindrically-shaped tube having a circular or semi-circular cross section. Other tubular configurations can include tubular shapes having other cross sections, including a triangle, square, pentagon, heptagon, octagon, other polygon, ellipses, oval, or other suitable cross sections. In some embodiments, as shown in FIG. 3, the port valve 60 consists only in a tube portion. FIG. 3 illustrates a perspective view of a cylindrically-shaped port valve 60, according to some embodiments.

As shown, the tube portion of the port valve 60 can be disposed at a location proximal the septum 70. As such, a portion of the septum activator 72 can extend through the tube portion of the port valve 60 prior to and during septum activation. Thus, the inner channel 64 of the port valve 60 can have an inner diameter that is larger than the outer diameter of the portions of the septum activator 72 that are disposed within the inner channel 64. As such, the septum activator 72 can move within the port valve without disturbing the port valve 60, which might result in unintentional opening of the port valve 60. Thus, the port valve 60 can provide an inner channel 64 through which a portion of the septum activator 72 can extend. The inner channel 64 can also provides a space into which a portion of the port valve 60 can collapse to open the port 50.

The tubular shape can also provide structural strength that maintains the outer surface 62 of the port valve 60 against the opening 54 in the absence of pressure from the port 50. The thickness of the walls of the tubular-shaped port valve 60 can be selected to adjust the predetermined pressure required to open the port valve 60. By increasing the thickness of the walls, a greater pressure is required to open the port valve 60. By decreasing the wall thickness, a smaller pressure is required to open valve 60. Additionally, the wall thicknesses can be adjusted based on the flexibility for rigidity the material forming the port valve 60. For instance, a more rigid valve may have thinner walls than those of a more flexible valve. Accordingly, the flexibility of the port valve 60 combined with the shape and size of the port valve 60 can determine, at least in part, the predetermined pressure required to open the port valve 60.

In various embodiments, the port valve 60 is seated within a groove or channel 94 (shown in FIG. 4), which comprises a recessed portion of the inner surface 78 of the catheter adapter 14. The outer diameter of the port valve 60 can be generally configured to compatibly and securely seat within the groove or channel 94. For example, in some embodiments, the outer diameter of the port valve 60 is selected to be both slightly smaller than the diameter of the groove or channel 94 and slightly larger than the diameter of the inner lumen 76. As such, the port valve 60 can be retained within the groove or channel 94 during use of the catheter assembly 10.

Specific reference will now be made to FIG. 4, which depicts a port valve that is combined with the septum to form a combined septum and port valve 90. The combined septum and port valve 90 can be an integrated structure that is formed of a single material as a single piece. As shown, the combined septum and port valve 90 can include a flexible tube portion that extends longitudinally about a longitudinal axis of the catheter adapter 14. The barrier member 75 of the septum can be substantially perpendicular to the flexible tube portion, or in other words, be disposed in a plane substantially perpendicular to the longitudinal axis of the catheter adapter 14.

This single piece combined septum and port valve 90 can minimize manufacturing costs and simplify the assembly procedure. Accordingly, the material selected for the combined septum and port valve 90 can accommodate the functional requirements of the septum and the port valve. In some embodiments, the combined septum and port valve 90 is formed in a common molding process. As further shown, the combined septum and port valve 90 can include various internal or external structures such as an inner ridge 92.

In use, the shape of the combined septum and port valve 90 can collapse under the force of a fluid being injected into the port 50. The collapsed shape provides a channel between the inner surface 78 of the catheter adapter 14 and outer surface 62 of the port valve 60. After the fluid infusion, into the catheter adapter 14, the port valve returns to its non-collapsed shape that closes the port 50. During fluid infusion through the catheter adapter 14, the pressure within the internal lumen 76 presses the port valve 60 against the opening 56, maintaining the port valve 60 closed.

For some infusion therapy techniques, airflow between the distal side and the proximal side of the septum 70 may be desirable. For example, for those embodiments comprising a septum 70 having a fluid-tight slit 74, passage of air from through the septum 70 is prohibited prior to opening or activating the septum 70 via the septum activator 72, as previously discussed. Thus, when the catheter 12 of the catheter assembly 10 is inserted into the vascular system of a patient, a positive pressure develops distal the septum 70 thereby preventing a desired flashback of the patient's blood into the catheter adapter 14. An observable flashback is generally desirable to confirm accurate placement of the catheter tip 20 within the vein of the patient. Thus, some embodiments of the present invention include features or elements to enable airflow between the distal side and the proximal side of the septum 70, without requiring activation of the septum 70 with the septum activator 72. As such, some embodiments of the present invention provide an observable flashback, as generally desired for infusion procedures.

For example, a plurality of air vent channels (not shown) can be interposed between the septum 70 and the inner surface 78 of the catheter adapter 14. The air vent channels can relieve the positive pressure distal the septum 70 by providing an access for air to bypass the septum 70 into the rearward chamber 64. In some embodiments, the air vent channels are constructed by removing portions of the surface of the channel 94, resulting in a plurality of generally parallel grooves.

In addition to permitting airflow between the distal side and the proximal side of the septum 70, the air vent channels may be configured to permit fluid to flow through the catheter adapter 14 prior to activating or opening the slit 74 with the septum activator 72. In some embodiments, the rate at which air and/or fluid flows is adjusted by manufacturing the catheter adapter 14 to include a greater or lesser number of air vent channels. In other embodiments, the rate at which air and/or fluid flows is adjusted by manufacturing the catheter adapter 14 to include air vent channels having a greater or lesser cross-sectioned area. Thus, in some embodiments the rate at which air and/or fluid flows is increased by manufacturing a catheter adapter 14 having either an increased number of vent channels, or vent channels having a greater cross-sectioned area. Conversely, in other embodiments, the rate at which air and/or fluid flows is decreased by manufacturing a catheter adapter 14 having either a decreased number of air vent channels, or air vent channels having a lesser cross-sectioned area.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly comprising:
   a catheter adapter forming an internal lumen that extends along a longitudinal axis of the catheter adapter, the catheter adapter having a distal end configured to couple to a catheter and a proximal end;
   a side port disposed on the catheter adapter, the side port forming an opening into the internal lumen of the catheter adapter;
   a septum disposed within the internal lumen of the catheter adapter, the septum comprising a barrier member that extends across the internal lumen perpendicular to the longitudinal axis thereby forming a seal between a distal portion and a proximal portion of the internal lumen, the barrier member being positioned distal to the side port;
   a port valve disposed within the internal lumen of the catheter adapter, the port valve comprising a flexible tube having an inner diameter and an outer diameter that is substantially the same as a diameter of the internal lumen, the port valve being positioned proximal to the barrier member and being positioned to cover the opening formed by the side port; and
   a septum activator positioned within the internal lumen proximal to the barrier member, the septum activator having a distal portion having an outer diameter that is less than the inner diameter of the flexible tube of the port valve, the distal portion of the septum activator extending through the port valve and being configured to extend through the barrier member to open a fluid pathway through the septum.

2. The catheter assembly of claim 1, wherein the port valve and the septum form an integrated, single-piece member.

3. The catheter assembly of claim 2, wherein the barrier member includes a slit therethrough.

4. The catheter assembly of claim 1, wherein the port includes a body that is generally oriented substantially perpendicularly to the longitudinal axis of the internal lumen.

5. The catheter assembly of claim 1, wherein the flexible tube of the port valve is a cylindrically-shaped tube.

6. The catheter assembly of claim 1, wherein the port valve is disposed within a recessed portion of the inner surface of the internal lumen of the catheter adapter such that the outer diameter of the flexible tube is substantially the same as the diameter of the recessed portion of the internal lumen.

7. A catheter assembly comprising:
   a catheter adapter forming an internal lumen that extends along a longitudinal axis of the catheter adapter, the catheter adapter having a distal end configured to couple to a catheter and a proximal end;

a side port disposed on the catheter adapter, the side port forming an opening into the internal lumen of the catheter adapter;

a blood control valve disposed within the internal lumen, the blood control valve comprising a septum and a septum activator positioned proximal to the septum, the septum comprising a barrier member that extends across the internal lumen perpendicular to the longitudinal axis thereby forming a seal between a distal portion and a proximal portion of the internal lumen, the barrier member being positioned distal to the side port; and a port valve disposed within the internal lumen proximal to the barrier member, the port valve comprising a flexible tube having an outer surface that covers the opening formed by the side port, the flexible tube having an inner diameter configured to allow a distal portion of the septum activator to extend through the flexible tube and bypass the barrier member.

8. The catheter assembly of claim 7, wherein the port valve and the septum of the blood control valve form an integrated, single-piece member.

9. The catheter assembly of claim 8, wherein the barrier member includes one or more slits.

10. The catheter assembly of claim 7, wherein the port includes a body that is generally oriented substantially perpendicularly to the longitudinal axis of the internal lumen.

11. The catheter assembly of claim 7, wherein the flexible tube is a cylindrically-shaped tube.

12. The catheter assembly of claim 7, wherein the port valve is a separate component from the septum.

13. The catheter assembly of claim 7, wherein the port valve is disposed within a recessed portion of the inner surface of the internal lumen of the catheter adapter.

14. The catheter assembly of claim 7, further comprising a port cover that covers the side port.

15. A catheter assembly comprising:

a catheter adapter having a distal end coupled to a catheter and a proximal end, the catheter adapter forming a lumen that extends from the distal end to the proximal end along a longitudinal axis, the catheter adapter further including a side port that forms an opening into the lumen;

a septum positioned within the lumen, the septum comprising a barrier member that extends across the internal lumen perpendicular to the longitudinal axis thereby forming a seal between a distal portion and a proximal portion of the internal lumen, the barrier member being positioned distal to the opening formed by the side port;

a flexible tube positioned within the lumen proximal to the barrier member such that an outer surface of the flexible tube covers the opening formed by the side port; and a septum activator positioned proximal to the barrier member, the septum activator having a distal portion that extends through the flexible tube and is configured to bypass the barrier member when the septum activator is moved distally.

* * * * *